US008778869B2

(12) United States Patent
Murphy et al.

(10) Patent No.: US 8,778,869 B2
(45) Date of Patent: Jul. 15, 2014

(54) TISSUE REGENERATION SYSTEM

(75) Inventors: William L. Murphy, Madison, WI (US); Mark D. Markel, Middleton, WI (US); Ben K. Graf, Madison, WI (US); Yan Lu, Fitchburg, WI (US); Jae Sung Lee, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 136 days.

(21) Appl. No.: 12/796,743

(22) Filed: Jun. 9, 2010

(65) Prior Publication Data
US 2011/0305760 A1  Dec. 15, 2011

(51) Int. Cl.
*A61K 38/00* (2006.01)
*A61K 38/16* (2006.01)
*A61K 38/17* (2006.01)
*A61K 38/18* (2006.01)
*A61K 9/00* (2006.01)
*A61K 8/64* (2006.01)

(52) U.S. Cl.
USPC ............... 514/1.1; 514/7.6; 514/8.1; 514/8.5; 514/8.8; 514/8.9; 514/9.1; 424/422; 424/423; 424/484; 424/491

(58) Field of Classification Search
None
See application file for complete search history.

(56) References Cited

U.S. PATENT DOCUMENTS

| 6,676,928 B2 | 1/2004 | Platzek et al. |
| 6,767,928 B1 | 7/2004 | Murphy et al. |
| 2008/0095817 A1 * | 4/2008 | Murphy ........................ 424/423 |

OTHER PUBLICATIONS

Cameron et al., http://www.ncbi.nlm.nih.gov/books/NBK6294/?report=printable, accessed Sep. 25, 2013.*
Duan, Y.R., et al., "Dynamic Study of Calcium Phosphate Formation on Porous HATCP Ceramics," J. Mater Sci. Mater Med., 16: 795-801 (2005).
Huang, X., et al., "Apatite Formation on the Surface of Wollastonite/Tricalcium Phosphate Composite Immersed in Simulated Body Fluid," J. Biomed Mater Res. B. Appl. Biomater, vol. 69B, 70-2 (2004).
Rohanizadeh, R., et al., Apatite Precipitation after Incubation of Biphasic Calcium-Phosphate Ceramic in Various Solutions: Influences of Seed Species and Proteins, J. Biomed Mater Res., 42: 530-9 (1998).
Xin, R., et al., "A Comparative Study of Calcium Phosphate Formation on Bioceramics in Vitro and in Vivo," Biomaterials, 26: 6477-86 (2005).
Edwards, R.B., "Percutaneous Injection of Recombinant Human Bone Morphogenetic Protein-2 in a Calcium Phosphate Paste Accelertes Healing of a Canine Tibial Osteotomy," J. Bone Joint Surg. Am. 86:1425-1438 (2004).
Hect, P., et al., "The Thermal Effect of Monopolar Radiofrequency Energy on the Properties of Joint Capsule. An in Vivo Histologic Study Using a Sheep Model," Am. J. Sports Med., 26: 808-14 (1998).
Lopez, M.J., "In Vivo Evaluation of Intra-Articlular Protection in a Novel Model of Canine Cranial Cruciate Ligament Mid-Substance Elongation Injury," Vet Surg., 35: 711-20 (2006).
Lu, Y., et al., "In Vivo Transplantation of Neonatal Ovine Neocartilage Allografts: Determining the Effectiveness of TissueTransglutaminase," J. Knee Surg., 18: 31-42 (2005).
Lu, Y., et al., "The Effect of Monopolar Radiofrequency Treatment Pattern on Joint Capsular Healing. In Vitro and in Vivo Studies Using an Ovine Model," Am. J. Sports Med., 28: 711-9 (2000).
Lu, Y., et al., "The Effect of Monopolar Radiofrequency Energy on Partial-Thickness Defects of Articular Cartilage, "Arthroscopy, 16: 527-36 (2000).
Lu, Y., et al., "Development of Partial Thickness Articular Cartilage Injury in an Ovine Model," J. Orthop Res., 24: 1974-82 (2006).
Kim, C.S., et al., "Ectopic Bone Formation Associated with Recombinant Human Bone Morphogenetic Proteins-2 Using Absorbably Collagen sponge and Beta Tricalcium Phosphate as Carriers," Biomaterials, 26: 2501-7 (2005).
Yamamoto, M., et al., "Controlled Release by Biodegradable Hydrogels Enhances the Ectopic Bone Formation of Bone Morphogenetic Protein," Biomaterials, 24: 4375-83 (2003).
Yamamoto, M., et al., "Ectopic Bone Formation Induced by Biodegradable Hydrogels Incorporating Bone Morphogenetic Protein," J. Biomater Sci Polym Ed., 9: 439-58 (1998).
Isobe, M., et al., "The Role of Recombinant Human Bone Morphogentic Protein-2 in PLGA Capsules at an Extraskeletal Site of the Rat," J. Biomed Mater Res., 45: 36-41 (1999).
Kessler, S., et al., "The Impact of Bone Morphogenetic Protein-2 (BMP-2), Vascular Endothelial Growth Factor (VEGF) and Basic Fibroblast Growth Factor (b-FGF) on Osseointegration Degradation and Biomechanical Properties of a Synthetic Bone Substitute," Z. O-Thop., vol. 141, 472-80 (2003).
Welch, R.D., et al., "Effect of Recombinant Human Bone Morphogenetic Protein-2 on Fracture Healing in a Goat Tibial Fracture Model," J. Bone Miner Res., 3: 1483-90 (1998).
Innocenti, M., et al., "Epiphyseal Transplant: Harvesting Technique of the Proximal Fibula Based on the Anterior Tibial Artery," Microsurgery, 25: 284-92 (2005).
Reed, A.A., et al., "Vascularity in a New Model of Atrophic Nonunion," J. Bone Joint Surg. Br., vol. 85-B, 604-10 (2003).
Welsh, E.M., et al., "Comparison of a Visual Analogue Scale and a Numerical Rating Scale for Assessment of Lameness, Using Sheep as a Model," Am. J. Vet. Res., 54: 976-83 (1993).
Quinn, M.M., et al., "Evaluation of Agreement Between Numerical Rating Scales, Visual Analogue Scoring Scales, and Force Plate Galt Analysis in Dogs," Vet Surg., 36: 360-7 (2007).
Furuya, Y., et al., "Computerized Tomography of Cranial Sutures. Part 2: Abnormalities of Sutures and Skull Deformity in Craniosynostosis," J. Neurosurg, 61: 59-70 (1984).
Adelaar, R.S., et al., Autologous Cortical Bone Grafts with Microsurgical Anastomosis of Periosteal Vessels, Surg Forum, 25: 487-9 (1974).

(Continued)

*Primary Examiner* — Elizabeth C Kemmerer
(74) *Attorney, Agent, or Firm* — Armstrong Teasdale LLP

(57) ABSTRACT

A system for growing tissue based upon layers of an inorganic extracellular matrix, wherein each layer of the inorganic matrix is designed to dissolve at a separate rate and result in sequential growth factor delivery upon its dissolution.

15 Claims, 10 Drawing Sheets

(56) References Cited

OTHER PUBLICATIONS

Beris, A.E., et al., "Non-Union of Femoral Neck Fractures with Osteonecrosis of the Femoral Head: Treatment with Combined Free Vascularized Fibular Grafting and Subtrochanteric Valgus Osteotomy," Orthop Clin North Am., 35: 335-43 (2004).
Malizos, K.N., "Free Vascularized Fibular Graft: A Versatile Graft for Reconstruction of Large Skeletal Defects and Revascularization of Necrotic Bone," Microsurgery, 13: 182-7 (1992).
Malizos, K.N., et al., "Longstanding Nonunions of Scaphoid Fractures with Bone Loss: Successful Reconstruction with Vascularized Bone Grafts," J. Hand Surg., 26B: 330-4 (2001).
Yancopoulos G., et al., "Vascular-specific growth factors and blood vessel formation," Nature 407:242-248 (2000).
Langer, R. & Moses, M., "Biocompatible controlled release polymers for delivery of polypeptides and growth factors," J. Cell Biochem. 45:340-345 (1991).
Langer, R., "New methods of drug delivery," Science 249:1527-1533 (1990).
Leong, K., et al., "Polyanhydrides for controlled release of bioactive agents," Biomaterials 7:364-371 (1986).
Cohen, S., et al., "Controlled delivery systems for proteins based on poly(lactic/glycolic acid) microspheres," Pharm. Res. 8:713-720 (1991).
Pekarek, K., et al., "Double-walled polymer microspheres for controlled drug release," Nature 367:258-260 (1994).
Lee, K., et al., "Controlled growth factor release from synthetic extracellular matrices," Nature 408:998-1000 (2000).
Tabata, Y. & Ikada, Y., "Vascularization effect of basic fibroblast growth factor released from gelatin hydrogels with different biodegradabilities," Biomaterials 20:2169-2175 (1999).
Anseth, K., et al., "In situ forming degradable networks and their application in tissue engineering and drug delivery," J. Control. Release 78:199-209 (2002).
Murphy, W., et al., "Sustained release of vascular endothelial growth factor from mineralized poly(lactide-co-glycide) scaffolds for tissue engineering," Biomaterials 21:2521-2527 (2000).
Murphy, W., et al., "Bone regeneration via a mineral substrate and induced angiogenesis," J. Dent. Res. 83:204-210 (2004).
Sheridan, M., et al., "Bioabsorbable polymer scaffolds for tissue engineering capable of sustained growth factor delivery," J. Control. Release 64:91-102 (2000).
Howdle, S. et al., "Supercritical fluid mixing: preparation of thermally sensitive polymer composites containing bioactive materials," Chemical Commun. 1:109-110 (2001).
Yang, X., et al., "Novel osteoinductive biomimetic scaffolds stimulate human osteoprogenitor activity—implications for skeletal repair," Connect. Tissue Res. 44:312-317 (2003).
Zisch, A., et al., "Covalently conjugated VEGF-fibrin matrices for endothelialization," J. Control. Release 72:101-113 (2001).
Raiche, A. & Puleo, D., "Cell responses to BMP-2 and IGF-I released with different time-dependent profiles," J. Biomed. Mater. Res. 69A:342-350 (2004).
Raiche, A. & Puleo, D., "In vitro effects of combined and sequential delivery of two bone growth factors," Biomaterials 25:677-685 (2004).
Gilbert, M., et al., "Chimeric peptides of statherin and osteopontin that bind hydroxyapatite and mediate cell adhesion," J. Biol. Chem. 275:16213-16218 (2000).
Stayton, P., et al., "Molecular recognition at the protein-hydroxyapatite interface," Crit. Rev. Oral Biol. Med. 14:370-376 (2003).
Harris, H., et al., "Functional analysis of bone sialoprotein: identification of the hydroxyapatite-nucleating and cell-binding domains by recombinant peptide expression and site-directed mutagenesis," Bone 27:795-802 (2000).
Tye, C., et al., "Delineation of the hydroxyapatite-nucleating domains of bone sialoprotein," J. Biol. Chem. 278:7949-7955 (2003).
Lin, H., et al., "Porous alginate/HAP sponges for bone tissue engineering," Materials Science Forum 426-432:343-3048 (2003).
Bunker, B., et al., "Ceramic thin film formation on functionalized interfaces through biomimetic processing," Science 264:48-55 (1994).
Ngankam, P.A., et al., "Influence of Polyelectrolyte Multilayer Films on Calcium Phosphate Nucleation," J. Am. Chem. Soc., 122, 8998-9005 (2000).
Lu, C., et al. "Ischemia Leads to Delayed Union During Fracture Healing: a mouse model," J. Orthop Res., 25: 51-61 (2007).
Einhorn, T.A., "Enhancement of Fracture-Healing," J. Bone Joint Sur. Am., 77: 940-56 (1995).
Ishaug-Riley, S.L., et al., "Ectopic Bone Formation by Marrow Stromal Osteoblast Transplantation Using Poly(DL-lactic-co-glycolic acid)Foams Implanted into the Rat Mesentery," J. Biomed Mater Res., 36: 1-8 (1997).
Ishaug, S.L., et al., "Bone Formation by Three-Dimensional Stromal Osteoblast Culture in Biodegradable Polymer Scaffolds," J. Biomed Mater Res., 37: 17-28 (1997).
Muschler, G.F., et al., "Engineering Principles of Clinical Cell-Based Tissue Engineering," J. Bone Joint Surg. Am., 86: 1541-58 (2004).
Insight, M., "Poor Man's" Bone Growth Factors: do they work?, Medtech Insight Newsletter, 263-264 (2003).
Lind, M., "Growth Factor Stimulation of Bone Healing. Effects on Osteoblasts, Osteomies, and Implants Fixation," Acta Orthop Scand Suppl., vol. 69, No. 283, 2-37 (1998).
Seeherman, H., "The Influence of Delivery Vehicles and their Properties on the Repair of Segmental Defects and Fractures with Osteogenic Factors," J. Bone Joint Surg. Am., vol. 83, S79-81 (2001).
Winn, et al., Sustained Release Emphasizing Recombinant Human Bone Morphogenetic Protein-2, Adv. Drug Deliv. Rev., 31: 303-318 (1998).
Colton, C.K., "Implantable Biohybrid Artificial Organs," Cell Transplant, vol. 4, No. 4, 415-36 (1995).
Prockop, D.J., "Marrow Stromal Cells as Stem Cells for Nonhematopoietic Tissues," Science, 276: 71-4 (1997).
Villars, F., et al., "Effect of Human Endothelial Cells on Human Bone Marrow Stromal Cell Phenotype: role of VEGF?," J. Cell Biochem., 79: 672-85 (2000).
Carmeliet, P., "Mechanisms of Angiogenesis and Arteriogenesis," Nat. Med., 6: 389-95 (2000).
Deckers, M.M., et al., "Bone Morphogenetic Proteins Stimulate Angiogenesis Through Osteoblast-Derived Vascular Endothelial Growth Factor," A. Endocrinology, vol. 143(4): 1545-53 (2002).
Gerber, H.P., et al., "VEGF Couples Hypertrophic Cartilage Remodeling, Ossification and Angiogenesis During Endochondral Bone Formation," Nat. Med., vol. 5, 623-8 (1999).
Hausman, M.R., et al., "Prevention of Fracture Healing in Rats by an Inhibitor of Angiogenesis," Bone, vol. 29, 560-4 (2001).
Eckardt, H., et al., "Recombinant Human Vascular Endothelial Growth Factor Enhances Bone Healing in an Experimental Nonunion Model," J. Bone Joint Surg., vol. 87-B,1434-8 (2005).
Street, J., et al., "Vascular endothelial Growth Factor Stimulates Bone Repair by Promoting Angiogenesis and Bone Turnover," Proc Natl. Acad. Sci. USA, vol. 99, 9656-61 (2002).
Peters, M.C., et al., "Engineering Vascular Networks in Porous Polymer Matrices," J. Biomed Mater Res., 60: 668-78 (2002).
Richardson, T.P., et al., "Polymeric System for Dual Growth Factor Delivery," Nat. Biotechnol., vol. 19, 1029-34 (2001).
Lee, K.Y., et al., "Comparison of Vascular Endothelial Growth Factor and Basic Fibroblast Growth Factor on Angiogenesis in SCID Mice," J. Control Release, vol. 87, 49-56 (2003).
Markel, M.D., "The Effect of Increasing Gap width on Localized Densitometric Changes Within Tibial Ostectomies in a Canine Model," Calcif Tissue Int., 54: 155-9 (1994).
Murphy, W.L., et al., "Bioinspired Growth of Crystalline Carbonate Apatite on Biodegradable Polymer Substrata," J. Am. Chem, Soc., vol. 124, 1910-7 (2002).
Kokubo, T., et al., "Bioactive Metals: Preparation and Properties," J. Mater Sci. Mater Med., 15: 99-107 (2004).
Kokubo, T., et al., "How Useful is SBF in Predicting in Vivo Bone Bioactivity?", Biomaterials, 27: 2907-15 (2006).
Murphy, W.L., et al., "Effects of a Bone-Like Mineral Film on Phenotype of Adult Human Mesenchymal Stem Cells in Vitro," Biomaterials, 26: 303-10 (2005).
De Aza et al., "Bioeutectic: a new ceramic material for human bone replacement," 1997, Biomaterials, vol. 18, No. 19, pp. 1285-1291.

* cited by examiner

TISSUE REGENERATION SYSTEM

STATEMENT REGARDING FEDERALLY SPONSORED RESEARCH AND DEVELOPMENT

This invention was made with United States government support under AR052893 awarded by the National Institutes of Health. The United States government has certain rights in this invention.

INCORPORATION OF SEQUENCE LISTING

A paper copy of the Sequence Listing and a computer readable form of the sequence listing provided herein, containing the file named "P09200US_ST25.txt", which is 17,722 bytes in size (measured in MS-DOS), and are herein incorporated by reference. This Sequence Listing consists of SEQ ID NOs:1-19.

BACKGROUND OF THE DISCLOSURE

This disclosure relates generally to a tissue regeneration system, and more particularly to a system that includes a template layered with one or more layers of an extracellular matrix, wherein the matrix layer includes one or more biomolecule(s) having a cell-affecting portion, and in some embodiments, a matrix-binding portion, and where the biomolecule is releasably associated with the matrix. In use, the matrix layer(s) degrade at various predictable rates, facilitating temporal control over release of the biomolecule(s) from the matrices.

One area of tissue regeneration that would benefit from improved biological surrogates is bone tissue regeneration systems. Under physiological conditions, bone tissue regeneration involves a complex interplay of multiple biologically active molecules and stem cells. The biologically active molecules are often presented sequentially in "cascades," where each factor has a distinct effect on the cells of a growing bone tissue. These biologically active molecules can be exploited to direct active regeneration of functional bone tissue for repair or for replacement. A key issue in designing systems to aid in bone tissue regeneration is to temporally control tissue concentration of biologically active molecules such as growth factors and/or cytokines.

Regenerating natural bone tissue represents a promising approach to bone replacement and could supplant many of the current, metallic, hardware-based bone replacement methods and expand the range of orthopedic conditions that can be effectively treated. Potential applications of novel bone regeneration systems include filling of bone voids in non-union fractures or maxillofacial deformities, bridging of gaps in spine fusion surgeries and stabilizing vertebral compression fractures. Not only would improved bone tissue regeneration systems offer an expanded range of treatment for orthopedic conditions, they would also be economically advantageous.

Existing passive bone tissue repairing or replacing systems do not exert a high level of control over the process of new bone formation. Such passive tissue regeneration systems include simply adding growth factors to a defect site in solution. However, such systems are inefficient because single growth factors delivered either by bolus injections into the site of disease or by systemic administration require very high levels for a measurable in vivo effect. In many instances, the growth factors will simply diffuse away from a defect site, leading to limited effects. Additionally, uncontrolled growth factor activity may occur at a distant site. See Yancopoulos G, et al., "Vascular-specific growth factors and blood vessel formation," Nature 407:242-248 (2000). To solve these problems, tissue regeneration systems embed growth factors into plastic microspheres, thereby localizing growth factors to a defect site. See Langer R & Moses M, "Biocompatible controlled release polymers for delivery of polypeptides and growth factors," J. Cell Biochem. 45:340-345 (1991); Langer R, "New methods of drug delivery," Science 249:1527-1533 (1990); Leong K, et al., "Polyanhydrides for controlled release of bioactive agents," Biomaterials 7:364-371 (1986); Cohen S, et al., "Controlled delivery systems for proteins based on poly(lactic/glycolic acid) microspheres," Pharm. Res. 8:713-720 (1991); and Pekarek K, et al., "Double-walled polymer microspheres for controlled drug release," Nature 367:258-260 (1994). None of these systems, however, provides a structural matrix for tissue ingrowth. In addition, these systems are difficult to process into structural matrices while retaining adequate biological activity of the growth factor. Furthermore, many of these systems have failed to demonstrate the ability to temporally deliver multiple growth factors.

Other tissue regeneration systems embed growth factors in hydrated gels, thereby localizing growth factors to a defect site. See Lee K, et al., "Controlled growth factor release from synthetic extracellular matrices," Nature 408:998-1000 (2000); Tabata Y & Ikada Y, "Vascularization effect of basic fibroblast growth factor released from gelatin hydrogels with different biodegradabilities," Biomaterials 20:2169-2175 (1999); and Anseth K, et al., "In situ forming degradable networks and their application in tissue engineering and drug delivery," J. Control. Release 78:199-209 (2002). However, like plastic microspheres, hydrated gels are not particularly well-suited for certain types of tissue regeneration because the growth factors rapidly diffuse out of the gel matrix, resulting in limited signaling. To overcome these problems, tissue regeneration systems have relied upon methods of gas foaming a porous plastic scaffold to allow for incorporation of growth factors with biological activity and variable release rates of several days to months. See Murphy W, et al., "Sustained release of vascular endothelial growth factor from mineralized poly(lactide-co-glycide) scaffolds for tissue engineering," Biomaterials 21:2521-2527 (2000); Murphy W, et al., "Bone regeneration via a mineral substrate and induced angiogenesis," J. Dent. Res. 83:204-210 (2004); Sheridan M, et al., "Bioabsorbable polymer scaffolds for tissue engineering capable of sustained growth factor delivery," J. Control. Release 64:94-102 (2000); Howdle S, et al., "Supercritical fluid mixing: preparation of thermally sensitive polymer composites containing bioactive materials," Chemical Commun. 1:1-2 (2001); and Yang X, et al., "Novel osteoinductive biomimetic scaffolds stimulate human osteoprogenitor activity—implications for skeletal repair," Connect. Tissue Res. 44:312-317 (2003). See also U.S. Pat. No. 6,676,928.

Similarly, others have used covalent conjugation of growth factors to hydrogels and multilayered hydrogels to provide enhanced control over osteogenic growth factor delivery. See Zisch A, et al., "Covalently conjugated VEGF-fibrin matrices for endothelialization," J. Control. Release 72:101-113 (2001); Raiche A & Puleo D, "Cell responses to BMP-2 and IGF-I released with different time-dependent profiles," J. Biomed. Mater. Res. 69A:342-350 (2004); and Raiche A & Puleo D, "In vitro effects of combined and sequential delivery of two bone growth factors," Biomaterials 25:677-685 (2004). These tissue regeneration systems, however, have not yet achieved satisfactory temporal control over cell activity while new tissue forms. In addition, these tissue regeneration systems have difficulty in temporally controlling the processing of heterogeneous and degradable materials with layers containing growth factors. Furthermore, none of these systems permits an adequate release of growth factors from a single matrix using release mechanisms that occur over distinct timeframes.

For the foregoing reasons, there is a need for a tissue regeneration system that localizes and temporally controls the release of multiple growth factors to stimulate tissue regeneration.

BRIEF SUMMARY

The present disclosure is summarized in that a system for regenerating tissue, including but not limited to bone, includes a template having layered therewith at least one synthetic, degradable extracellular matrix layer, where at least one layer has associated therewith (i.e. therein, thereon or both), at least one biomolecule having a cell-affecting portion via Van der Waals forces. In another embodiment, the biomolecule is releasably associated with the matrix layer via a matrix-binding portion. In use, extracellular matrix layers dissolve and degrade under physiological conditions at predictable rates to facilitate release of the biomolecule. The released biomolecule is bioactive and is in sufficiently close proximity to one or more cell types of interest to advantageously affect a cell-mediated bioactivity. When the system includes two or more matrix layers having distinct structural attributes, the layers can degrade at distinct rates. When distinct layers include distinct biomolecules, each biomolecule release can be temporally controlled.

In one particular aspect, the system includes a porous template consisting of β-tricalcium phosphate and having thereupon at least one synthetic, degradable extracellular matrix layer, and at least one biomolecule releasably associated with the matrix layer. The biomolecule includes a cell-affecting portion. The β-tricalcium phosphate template advantageously allows for a similar structure and composition to natural bone mineral, and further provides improved control of matrix mineral dissolution and biomolecule release. This temporal control is provided by varying the amount of biomolecule present during the template coating process and/or varying the coating thickness of the matrix layer. Accordingly, the tissue regeneration system may be used for modulating the degradation rate of a porous template of β-tricalcium phosphate. In some embodiments, the tissue regeneration system comprises a porous template consisting of β-tricalcium phosphate and having thereupon at least one synthetic, degradable extracellular matrix layer.

In some embodiments, the extracellular matrix layer includes a biomolecule that does not natively interact with the matrix layer. In other embodiments, the extracellular matrix layer includes a biomolecule that natively interacts with the matrix layer.

In some embodiments, the matrix layer attracts the cells to the tissue regeneration system, in vivo or in vitro. In some embodiments, in vivo or in vitro, the cells associate with an outer surface of the matrix layer-coated template. When the template is porous, the cells can associate with the pores of the template.

In some embodiments, the biomolecule additionally includes a matrix-binding portion. The matrix-binding portion of the biomolecule is a calcium-binding protein or a calcium-binding portion of the calcium-binding protein. In other embodiments, the matrix-binding portion of the biomolecule is SEQ ID NO:1. In still other embodiments, the matrix-binding portion of the biomolecule includes at least one of SEQ ID NO:2, SEQ ID NO:3, SEQ ID NO:12, SEQ ID NO:13, SEQ ID NO:14, SEQ ID NO:15, SEQ ID NO:16, and SEQ ID NO:17.

In another aspect, the disclosure is summarized in that a method for making a degradable extracellular matrix layer includes the step of combining, in a solution at a physiological temperature and a physiological pH, at least one species of biomolecule having a cell-affecting portion and inorganic mineral ions, in the presence of a template having polar oxygen groups until a first inorganic mineral matrix layer containing matrix-associated biomolecules is deposited on the template surface.

In yet another aspect, the disclosure is summarized in that a method for making a degradable extracellular matrix layer includes the steps of exposing inorganic mineral ions in a solution at a physiological temperature and a physiological pH to a template having polar oxygen groups on a surface thereof until an inorganic mineral matrix layer is deposited on the surface, and exposing at least one species of biomolecule having a cell-affecting portion to the layer until the layer has associated therewith the at least one species of biomolecule.

In one aspect, the method includes coating a template with the degradable extracellular matrix layer including at least one biomolecule. The matrix layer is formed by exposing ions of an inorganic mineral in a solution at a physiological temperature and pH to the template until an inorganic mineral matrix layer is deposited on the surface as described above. Further, at least one species of biomolecule having a cell-affecting portion is exposed to the matrix layer until the matrix layer has associated therewith the at least one species of biomolecule. In one aspect, the template consists of β-tricalcium phosphate.

In certain embodiments, the polar oxygen groups can be carboxylic acids, phosphates, aldehydes, ketones, alcohols, carbonyls, hydroxyls or metal oxides. For example, in one particular embodiment, the template includes phosphates on the surface and is β-tricalcium phosphate.

In certain other embodiments, the template can be polycarboxylates, polyanhydrides, poly(α-hydroxy esters), poly(ethylene terephthalate), poly(carbonates), poly(amides), poly(lactones), poly(saccharides) or poly(acrylates).

In certain embodiments, the aforementioned method steps are repeated at least twice, or both method steps are performed serially in either order, to deposit on the template a plurality of extracellular matrix layers containing, or having provided therewith, matrix-associated biomolecules. Additionally, the mineral ions and the biomolecule can be exposed to the template together, such that the biomolecule is integrated into the matrix layer as it forms. Relatedly, a biomolecule can be provided on a surface of the degradable extracellular matrix layer and a second matrix layer can be provided on the first matrix layer to embed the biomolecule into a specific portion of the layered structure. The skilled person will appreciate that one in possession of this disclosure can produce a wide variety of layered configurations engineered for use under a variety of conditions, as will become apparent from the disclosure infra. In producing separate layers in a multi-layer system, the conditions under which the components are combined, and/or amount of components can be varied to yield distinct matrix layers having structures and dissolution properties distinct from the other layers.

The described embodiments of the present disclosure have many advantages, including that the materials are biocompatible and that all steps can be carried out at physiological temperatures and at physiological pH to maintain activity of the biologically active molecule.

It is an object of the present disclosure to temporally control growth factor signaling and thereby direct activities of associated cells, such as stem cells.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

Figure 1A:
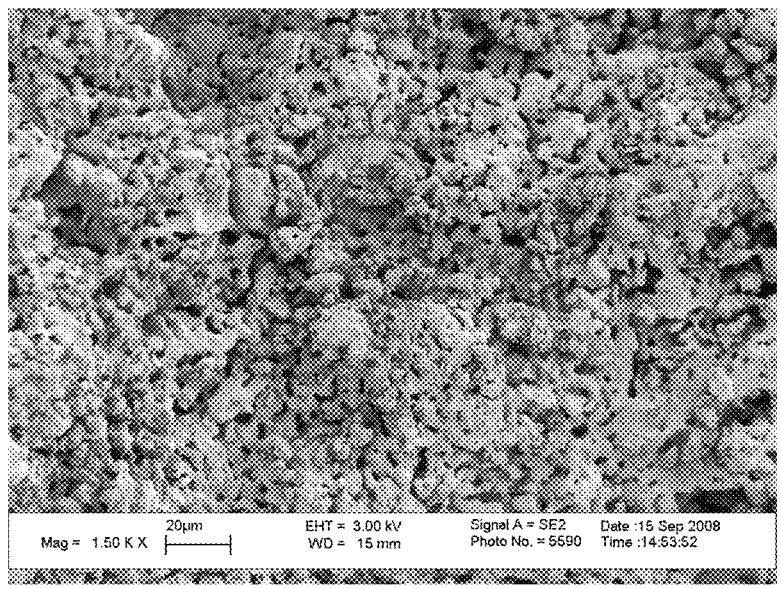
FIG. 1A is a low resolution scanning electron micrograph of β-tricalcium phosphate template without a matrix layer.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF PREFERRED EMBODIMENTS

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, suitable methods and materials are described below.

Suitable template materials are advantageously organic and advantageously contain side chains having carboxylic acid groups that induce mineral layer nucleation and growth or can undergo hydrolytic degradation to provide such side chain groups. Aspartic acid and/or glutamic acid residues on the templates, are particularly advantageous in that both residues include a carboxylic acid side chain. These include polycarboxylates, polyanhydrides, poly(α-hydroxy esters), poly(ethylene terephthalate), poly(carbonates), poly (amides), poly(lactones), poly(saccharides) and poly(acrylates). Other suitable template materials include materials having polar oxygen groups at the surface. The polar oxygen groups can be carboxylic acids, phosphates, aldehydes, ketones, alcohols, carbonyls, hydroxyls or metal oxides.

The template materials are advantageously macroporous and have a molecular weight sufficiently high to allow for formation of a template. The template materials need not be porous. For example, the template can be a non-porous surface such as a spherical surface formed of, e.g., α-hydroxy esters, on which mineral matrix layer nucleation and growth can occur. Other template surfaces for mineral matrix layer nucleation can include metallic surfaces, such as titanium or other like metals known to be suited for use in implants.

In one particularly preferred embodiment, the template is formed of β-tricalcium phosphate. The β-tricalcium phosphate is in the form of granules having a wide variety of particle sizes. For example, the particle size range of the β-tricalcium phosphate can range from tens of nanometer to several millimeters.

Figure 1B:
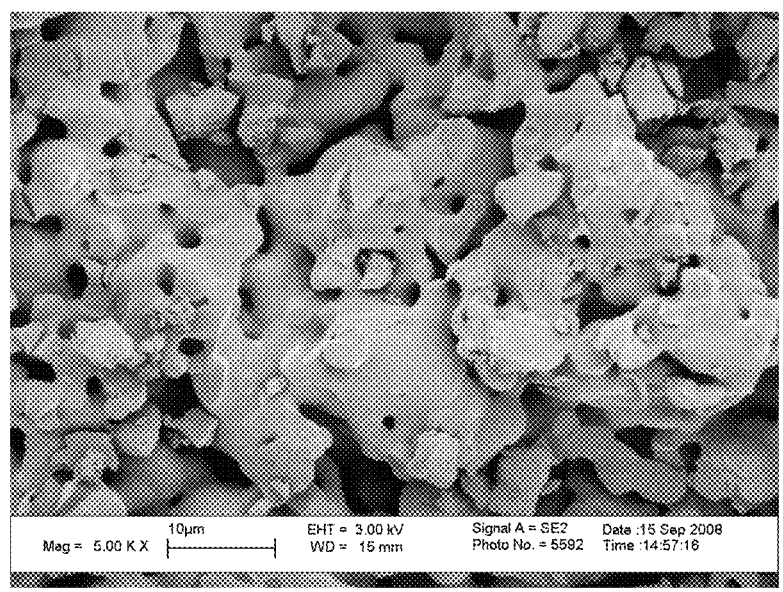
FIG. 1B is a high resolution scanning electron micrograph of β-tricalcium phosphate template without a matrix layer.

When a porous β-tricalcium phosphate template is used, the pore size varies from hundreds of nanometer to several hundreds of micrometer. FIGS. 1A and 1B are scanning electron micrographs showing an example of suitable porous β-tricalcium phosphate granules for use as the template (obtained from Berkeley Advanced Biomaterials, Berkeley, Calif.).

As described above, the template includes one or more extracellular matrix layers deposited thereon. The extracellular matrix layer can include a bone-mineral matrix. Inorganic minerals suitable for producing a bone-mineral matrix layer include bone mineral ions, such as, but not limited to calcium, carbonate, and phosphate and combinations of bone mineral ions, such as calcium-phosphates. The bone mineral matrix layer can include, e.g., hydroxyapatite (HAP), carbonate-substituted hydroxyapatite, α-tricalcium phosphate (α-TCP), β-tricalcium phosphate (β-TCP), amorphous calcium phosphate, dicalcium phosphate, octacalcium phosphate or calcium carbonate. Where the extracellular matrix includes a plurality of layers, separate layers having distinct dissolution profiles can be constructed upon the template. To control dissolution order, and, ultimately, delivery of the biomolecule(s), distinct layers are deposited upon the template. Under physiological conditions, solubility of calcium phosphate species adhere to the following trend: amorphous calcium phosphate>dicalcium phosphate>octacalcium phosphate>β-TCP>HAP. A dicalcium phosphate mineral will typically have a dissolution rate that is more than fifty times higher than that of HAP. Therefore, creation of a matrix with distinct calcium phosphate layers allows for a broad range of dissolution patterns.

Each layer can contain therein or thereon an active biomolecule releasably associated with the matrix layer. As used herein, "releasably associated", "releasably associating" and "releasably associated with" refers to the ability of a biomolecule that is covalently or non-covalently associated with a matrix layer to release from the matrix layer. Thus, upon dissolution of the matrix layer, the biomolecule becomes freely diffusible permitting the controlled delivery of the biomolecule. Additionally, dissolving layers containing no biomolecule can be included among the matrix layers to provide a delay between release of biomolecules or for other reasons. Suitable active biomolecules have a cell-affecting portion. Other suitable biomolecules have a cell-affecting portion and a matrix-binding portion covalently or non-covalently associated with the cell-affecting portion.

Biomolecules may be produced according to methods known in the art. For example, biomolecules may be purified or isolated nucleic acids, purified or isolated proteins, expressed proteins and fragments thereof produced according to recombinant protein expression methods, and peptides produced by peptide synthesis methods. A biomolecule may be made by recombinant methods by cloning cDNA encoding a cell-affecting portion. A biomolecule may be made by recombinant methods by cloning cDNAs encoding a cell-affecting portion, a spacer portion, and, if present, a matrix-binding portion in frame into an expression vector. More particularly, a biomolecule, having a sequence of SEQ ID NO:19, may be made by cloning a cDNA encoding the amino acid sequence of SEQ ID NO:8, as an example of a cell-affecting portion, in frame with a cDNA encoding the amino acid sequence of the SEQ ID NO:10, as an example of a spacer portion, and further in frame with a cDNA encoding the amino acid sequence of the hydroxyapatite binding peptide of SEQ ID NO:12, as an example of a matrix-binding portion. A biomolecule may also be made by cloning cDNAs for a cell-affecting portion and a matrix-binding portion in frame into an expression vector. For example, a biomolecule, having the sequence of SEQ ID NO:18, may be made by cloning a cDNA encoding the amino acid sequence of SEQ ID NO:8 in frame with a cDNA encoding the amino acid sequence of the hydroxyapatite binding peptide of SEQ ID NO:12. The expression vector is then used in protein expression systems such as, for example, bacteria, yeast, baculovirus/insect, and mammalian cells. If desired, the expressed protein may be purified and/or isolated according to methods known in the art such as, for example, precipitation, centrifugation, chromatography, and electrophoresis.

In some embodiments, the matrix-binding portion of the active biomolecules are amino acid sequences rich in glutamic acid, aspartic acid or phosphoserine, which interact directly with calcium ions in mineralized extracellular matrices and which are recognized in the art as binding well to bone minerals. See Gilbert M, et al., "Chimeric peptides of statherin and osteopontin that bind hydroxyapatite and mediate cell adhesion," J. Biol. Chem. 275:16213-16218 (2000); and Stayton P, et al., "Molecular recognition at the protein-hydroxyapatite interface," Crit. Rev. Oral Biol. Med. 14:370-376 (2003), each incorporated by reference in its entirety as if set forth herein. Particular amino acid sequences include EPRREVCEL (SEQ ID NO: 1), a matrix-binding fragment of osteocalcin, or SEQ ID NO:1 altered by extension to a length of at least about thirteen amino acids, for example with a series of heterotypic or homotypic residues (such as alanine, cysteine, leucine, methionine, glutamate, glutamine, histidine or lysine) that urge the matrix-binding portion into a preferred helical configuration. Likewise, matrix-binding fragments comprising at least about eight consecutive glutamic acid residues, e.g., EEEEEEEE (SEQ ID NO: 2) or at least about eight consecutive aspartic acid residues, e.g., DDDDDDDD (SEQ ID NO: 3) are contemplated. Harris H, et al., "Functional analysis of bone sialoprotein: identification of the hydroxyapatite-nucleating and cell-binding domains by recombinant peptide expression and site-directed mutagenesis," Bone 27:795-802 (2000); and Tye C, et al., "Delineation of the hydroxyapatite-nucleating domains of bone sialoprotein," J. Biol. Chem. 278:7949-7955 (2003). Other bone proteins, such as, but not limited to, matrix Gla protein (MGP), bone sialoprotein, phosphoryn and osteonectin may also contain suitable matrix-binding sequences.

In other embodiments, the matrix-binding portion may be a hydroxyapatite binding portion. Suitable hydroxyapatite binding portions may be, for example, XPRRXVAXL (SEQ ID NO:12) wherein X is Gla; XPRRAVAXL (SEQ ID NO:13) wherein X is Gla; XPRRAVAAL (SEQ ID NO:14) wherein X is Gla; EPRREVAEL (SEQ ID NO:15); EPRRAVAEL (SEQ ID NO:16); and EPRRAVAAL (SEQ ID NO:17).

As used herein, "cell-affecting portion" refers to the portion of the biomolecule that is capable of producing a response or reaction in or by a cell. The cell-affecting portion of the biomolecule can include, e.g., a growth factor, a hormone, a cytokine, a nucleic acid molecule or a biologically-active portion of any of the foregoing, such as a bioactive motif. Suitable growth factors can include growth factors affecting differentiation, proliferation, migration or other cell activities. Other suitable growth factors may be, for example, those that are capable of initiating osteogenesis, neovascularization, endothelial differentiation, and osteogenic differentiation, including, but not limited to, bone morphogenic protein, fibroblast growth factor, growth differentiation factor, platelet-derived growth factor, placental growth factor, transforming growth factor, and insulin-like growth factor. For example, bone morphogenetic protein-2 (BMP-2; SEQ ID NO:4) and fibroblast growth factor-2 (FGF-2; SEQ ID NO:5) are suitable cell-affecting portions, as are portions or motifs thereof that retain the growth factor activity. Other examples include bone morphogenetic protein-7 (BMP-7; SEQ ID NO:6) and vascular endothelial growth factor (VEGF; SEQ ID NO:7). Yet other examples of suitable cell-affecting portions may include, for example, the peptide sequence KIP-KASSVPTELSAISTLYL (SEQ ID NO:8) and the peptide sequence KLTWQELYQLKYKGI (SEQ ID NO:9).

Cell-affecting portions of the biomolecule may or may not natively interact with the matrix-layer. For example, bone sialoprotein, phosphoryn and osteonectin contain suitable mineral-binding sequences that natively interact with a matrix layer such as hydroxyapatite. Other cell-affecting portions, such as, for example, platelet derived growth factor and fibroblast growth factor do not contain sequences known to natively interact with a matrix layer such as hydroxyapatite.

In some embodiments, the biomolecule may include a spacer portion. The spacer portion provides additional distance or separation between the matrix-binding portion and the cell-affecting portion of the biomolecule. It is believed that the bioactivity of the cell-affecting portion of the biomolecule may be increased with an increase in the spacer length. The additional length provided by spacer portion may also permit the cell-affecting portion of the biomolecule to function on the cell or cells while associated with the matrix or before the matrix has dissolved such that the biomolecule is released from the matrix. It is hypothesized that too little of a spacing between the surface of the matrix and the cell-affecting portion of the biomolecule may not be optimal as the cell-affecting portion may be so close to the matrix layer surface as not to be readily accessible to cell receptors. Accordingly, by controlling the spacing between the cell-affecting portion and the matrix-binding portion, the level of activity of the cell-affecting portion may be controlled.

Suitable spacer portions of the biomolecule may be, for example, amino acid sequences capable of forming an α-helix. Other suitable spacer portions may be, for example, AAAA (SEQ ID NO:10); GGGAAAA (SEQ ID NO:11); or one of $(A)_n$, $(E)_n$, $(K)_n$, and $(L)_n$, wherein n is an integer between 1 and 8. Other suitable spacer portions may be polyethylene glycol. Suitable polyethylene glycol spacer portions may be, for example, 3500 Da polyethylene glycol and 5000 Da polyethylene glycol.

In one embodiment, a suitable biomolecule is SEQ ID NO:18, having the cell-affecting portion of SEQ ID NO:8 and the matrix-binding portion of SEQ ID NO:12. In another embodiment, the biomolecules may include a spacer portion in addition to the cell-affecting portion and the matrix-binding portion. For example, one particularly suitable biomolecule is SEQ ID NO:19, which is formed of the cell-affecting portion of SEQ ID NO:8, a spacer portion (SEQ ID NO:10), and the matrix-binding portion of SEQ ID NO:12.

In some embodiments, the biomolecule may intrinsically have both a mineral-binding portion and a cell-affecting portion.

In use, bone tissue is regenerated in a subject having at a bone site an injury, a disease or a birth defect by providing the tissue regeneration system in or by directing the system to the site of the injury, disease or birth defect, whereupon the inorganic mineral layers sequentially dissolve, each layer's dissolution being dictated by the composition of its matrix.

The extracellular matrix layers described herein are developed by incubating the constituents in a "simulated body fluid" (SBF) or a "modified simulated body fluid" (mSBF) for five days or more at a pH of about 6.8 to about 7.4 and at a temperature of about 37° C. The SBF or mSBF is refreshed daily. This procedure produces a calcium-deficient, carbonate-containing apatite material on alginate and on poly-(α-hydroxy esters). See U.S. Pat. No. 6,767,928, incorporated herein by reference as if set forth in its entirety, for composition of SBF. mSBF includes elevated calcium and phosphate, as detailed infra. In general, an increase in pH favors hydroxyapatite growth, while a decrease in pH favors octacalcium phosphate mineral growth.

For example, conditions favorable for hydroxyapatite formation include a pH between about 5.0 and about 8.0 and a calcium concentration multiplied by a phosphate concentration between about $10^{-5}$ and about $10^{-8}$ M. Likewise, conditions favorable for octacalcium phosphate formation include a pH between about 6.0 and about 8.0 and a calcium concentration multiplied by a phosphate concentration between about $10^{-5}$ and about $10^{-7.5}$ M. Furthermore, conditions favorable for dicalcium phosphate dehydrate formation include a pH between about 6.0 and about 8.0 and a calcium concentration multiplied by a phosphate concentration between about $10^{-4}$ and about $10^{-6}$ M.

Specifically, using poly-(α-hydroxy esters) or alginate hydrogels as a template, one would vary the pH of mSBF between about 5.0 and about 6.0 to promote hydroxyapatite formation. Similarly, one would vary the pH of mSBF between about 6.0 and about 6.5 to promote octacalcium phosphate and hydroxyapatite formation. Likewise, one would vary the pH of mSBF between about 6.5 and about 8.0 to promote dicalcium phosphate, octacalcium phosphate and hydroxyapatite formation.

EXAMPLES

Example 1

Matrices with an Organic Template and Two Inorganic Mineral Layers Embedded with Distinct Biologically Active Molecules At least two calcium phosphate-based mineral layers, each having a distinct dissolution pattern and having a distinct growth factor, are engineered into/onto an organic template. Standard alginate processing methods are used to crosslink alginate with calcium, resulting in a solid hydrogel template having a high density of carboxylic acid groups is formed. The template is freeze-dried until the hydrogel undergoes a phase separation and develops large, interconnected macropores (50-200 μm). See Lin H, et al., "Porous alginate/HAP sponges for bone tissue engineering," Materials Science Forum 426-432:343-3048 (2003), incorporated herein by reference as if set forth in its entirety.

After processing, a HAP layer having a cross-sectional height of about 10 μm to about 1000 μm, is deposited on the hydrogel template at a physiological temperature in the range of about 35° C. to about 39° C. and at a physiological pH between about 5 and about 10 for 1 to 30 days, while retaining the macroporous structure of the template. The hydrogel template is incubated in a first mSBF solution containing ionic constituents of blood plasma, to initiate growth of a HAP layer, plus elevated levels of calcium (about 2.5 mM to about 25 mM) and phosphate (about 1 mM to about 10 mM) relative to conventional SBF, as well as a BMP-2 peptide (SEQ ID NO: 4) engineered using conventional methods to include the bone-mineral-binding sequence (SEQ ID NO: 1) at its C-terminal end. See U.S. Pat. No. 5,767,928, incorporated herein by reference as if set forth in its entirety; see also Bunker B, et al., "Ceramic thin film formation on functionalized interfaces through biomimetic processing," Science 264:48-55 (1994); and Ngankam P, et al., "Influence of polyelectrolyte multilayer films on calcium phosphate nucleation," J. Am. Chem. Soc. 122:8998-9004 (2000). Additionally or optionally, the octacalcium layer could include a BMP-7 peptide (SEQ ID NO: 6) engineered using conventional methods to include the bone-mineral-binding sequence (SEQ ID NO: 1) at its C-terminal end.

After production of the HAP layer, an octacalcium phosphate layer having a cross-sectional height of about 10 μm to about 100 μm is deposited on the HAP layer at a physiological temperature in the range of about 35° C. to about 39° C. at a physiological pH between about 6 and about 8 for 1 to 30 days, while retaining the macroporous structure of the template. The template with HAP layer is incubated in a second mSBF solution containing ionic constituents of blood plasma to initiate growth of the octacalcium phosphate layer, plus elevated levels of calcium (about 2.5 mM to about 25 mM) and phosphate (about 1 mM to about 10 mM) relative to conventional SBF, as well as an FGF-2 peptide (SEQ ID NO: 5) engineered using conventional methods to include the bone-mineral-binding sequence (SEQ ID NO:1) at its C-terminal end. Additionally or optionally, the HAP layer could include a VEGF peptide (SEQ ID NO: 7) engineered using conventional methods to include the bone-mineral-binding sequence (SEQ ID NO:1) at its C-terminal end.

Following the second incubation, the hydrogel template has coated thereupon the inner HAP layer containing the engineered BMP-2 peptide and the outer octacalcium phosphate layer containing the engineered FGF-2 peptide. Each layer can contain a plurality of bioactive molecules, or no bioactive molecule, as desired.

FGF-2 and BMP-2 each display optimal in vitro biological activity at approximately 1 nM. The low optimal concentrations coupled with the ability to deliver the growth factors in a sustained manner over time permits inclusion of miniscule amounts of growth factors into a growing mineral matrix. This small amount of total protein included into the matrix avoids significant interference with mineral growth, as interference with mineral growth by acidic proteins typically occurs at higher protein concentrations.

The dissolution patterns of the HAP and octacalcium phosphate layers establish the rate of growth factor release from the matrix, which is a key parameter in controlling cell activity within the matrix. To establish the dissolution pattern, one varies the layers of mineral growth within the hydrogel template by systematically varying calcium concentration and pH. One should expect that a calcium concentration near that of blood plasma (2.5 mM) would result in formation of an HAP. Therefore, variations in calcium concentrations lead to formation of distinct calcium phosphate mineral layers. Other factors including, but not limited to, ionic concentrations of the solution, pH, surface energy of the template material and temperature can affect the type of calcium phosphate mineral layers.

Example 2

Temporal Control Over Mesenchymal Stem Cell Activity Via Sequential Growth Factor Release A. This example describes an important new approach to control in vitro and in vivo bone regeneration, by specifically demonstrating that the matrices of the invention can control stem cell activity in regenerating bone tissue by delivering growth factors that drive proliferation (FGF-2) and then differentiation (BMP-2) of mesenchymal stem cells (MSC) into functional osteoblasts. BMP-2 and FGF-2 have been chosen for their ability to elicit specific MSC activities and their importance in bone development and repair.

B. MSC are seeded into the octacalcium phosphate/HAP layered matrices of Example 1. The matrices deliver FGF-2 over one week in culture. At twenty-four hour intervals after initial cell seeding, cells are removed from the scaffolds via trypsinization and counted. To demonstrate cell proliferation in response to FGF-2, total cell number in matrices releasing FGF-2 is compared to cell number in control matrices without growth factor.

MSC cultured in matrices releasing FGF-2 retain their ability to differentiate down multiple lineages. To confirm the specific effect of FGF-2 on MSC proliferation, cell populations removed from the FGF-2-releasing matrices via trypsinization are cultured for seven days. The cells are replated in culture and are induced to differentiate into chondrocytes, adipocytes and osteoblasts. The methods to analyze differentiation of MSC into osteoblasts (alizarin red staining of mineral), adipocytes (oil red 0 staining of lipid vacuoles) and chondrocytes (staining of type II collagen matrix) are known to the skilled artisan and cocktails for induction of differentiation are commercially available (Cambrex, Inc. Baltimore, Md.).

C. Response of Mesenchymal Stem Cells to BMP-2 Delivery: MSC are seeded into octacalcium phosphate/HAP layered matrices wherein no FGF-2 is provided in the octacalcium phosphate layer. The matrices, therefore, release no growth factor for one week and then release BMP-2 from the HAP layer for four weeks. During the BMP-2 release period, matrices are analyzed for osteogenic activity at five day intervals. Matrices are demineralized, paraffin-embedded, sectioned, stained for bone matrix deposition and imaged using an Olympus IX-71 microscope with a Hamamatsu 285 digital camera Immunostaining for bone sialoprotein, OCN and osteonectin identifies regions of bone matrix deposition. Sections are also stained with Goldner's Trichrome, which stains osteoid red and mature bone matrix bright green. Additionally, the density of positively stained tissue grown within the matrices is quantified using Simple PCI image analysis software (Hamamatsu, Inc. Tokyo, JP).

D. Sequential Delivery of FGF-2 and BMP-2 to Mesenchymal Stem Cells In Vitro: MSC are incubated in mesenchymal stem cell growth medium at 37° C., pH 7.4, with 5% $CO_2$ and 95% humidity with matrices designed to release FGF-2 (one to ten days) followed by BMP-2 (four weeks) and analyzed for deposition of bone matrix as described previously. Bone matrix deposition is observed. Increasing the timeframe of FGF-2 release increases the total number of MSC and results in a larger population of cells capable of responding to BMP-2 induction. Accordingly, total bone matrix deposition increases with increased FGF-2 delivery.

Example 3

Tissue Regeneration System of β-TCP Template with a Hydroxyapatite Matrix Layer

In this Example, a tissue regeneration system was prepared using a porous β-tricalcium phosphate (β-TCP) template. The β-TCP template was coated with a hydroxyapatite (HAP) matrix layer. To prepare the tissue regeneration system consisting of a β-TCP template, β-TCP granules were incubated at 37° C. in modified simulated body fluid (mSBF; 141 mM NaCl 4 mM KCl, 0.5 mM $MgSO_4$, 1.0 mM $MgCl_2$, 5.0 mM $CaCl_2$, 1.0 mM $KH_2PO_4$, 20 mM Tris base, pH 6.8) containing 4.2 mM (Reg mSBF), 25 mM, 50 mM, or 100 mM $NaHCO_3$. Controls were incubated in mSBF without $NaHCO_3$.

Figure 2A:
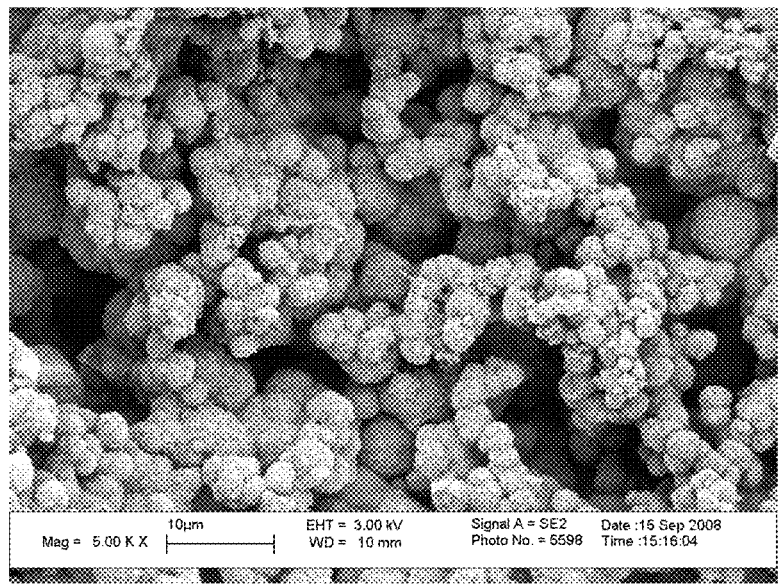
FIG. 2A is a low resolution scanning electron micrograph showing the matrix layer formed on the surface of a β-tricalcium phosphate template incubated for two days in mSBF containing 4.2 mM $NaHCO_3$.
Figure 2B:
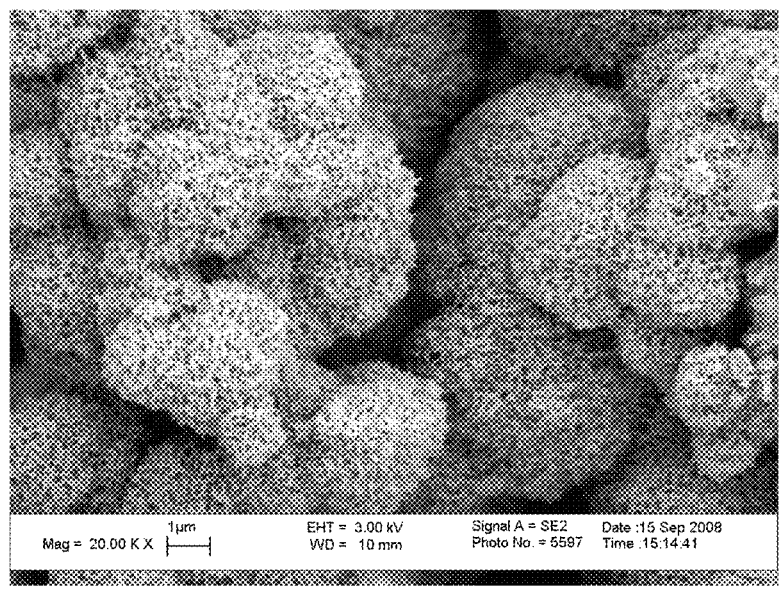
FIG. 2B is a high resolution scanning electron micrograph showing the matrix layer formed on the surface of a β-tricalcium phosphate template incubated for two days in mSBF containing 4.2 mM $NaHCO_3$.
Figure 3A:
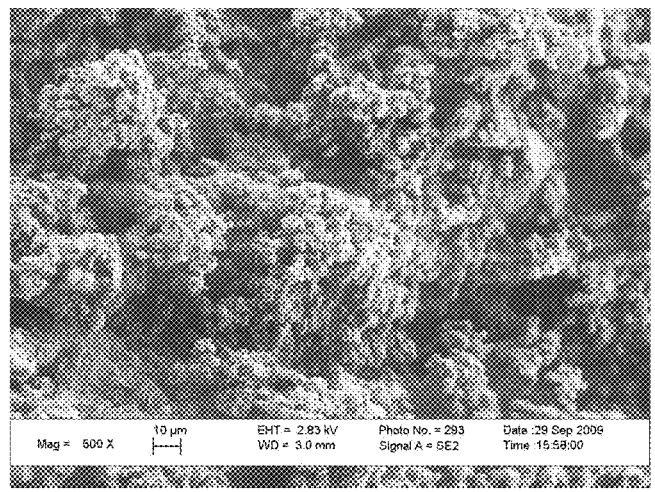
FIG. 3A is low resolution scanning electron micrograph showing the matrix layer formed on the surface of a β-tricalcium phosphate template incubated for seven days in mSBF containing 4.2 mM $NaHCO_3$.
Figure 3B:
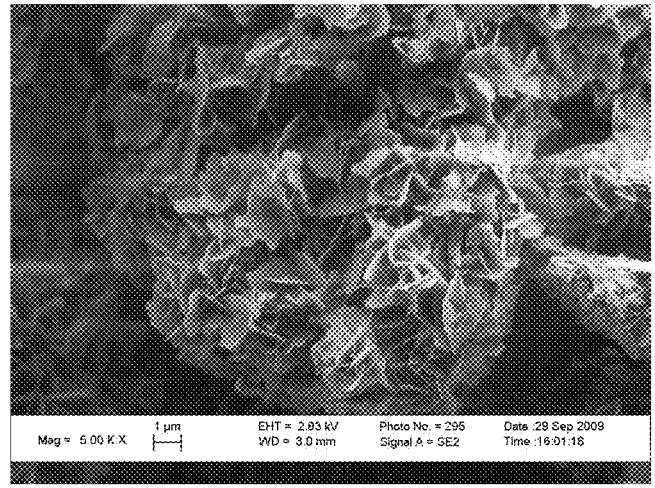
FIG. 3B is a high resolution scanning electron micrograph showing the matrix layer formed on the surface of a β-tricalcium phosphate template incubated for seven days in mSBF containing 4.2 mM $NaHCO_3$.
Figure 3C:
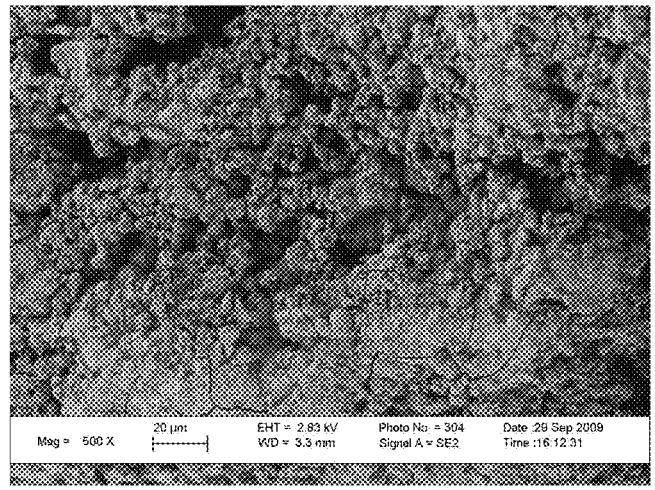
FIG. 3C is a low resolution scanning electron micrograph showing the matrix layer formed on the surface of a β-tricalcium phosphate template incubated for seven days in mSBF containing 100 mM $NaHCO_3$.
Figure 3D:
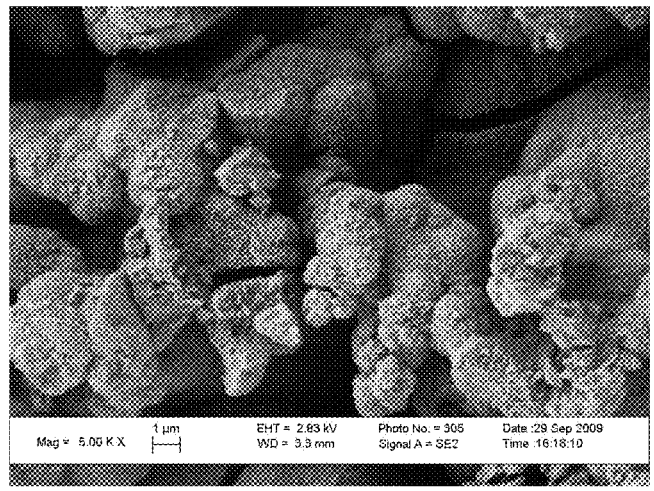
FIG. 3D is a high resolution scanning electron micrograph showing the matrix layer formed on the surface of a β-tricalcium phosphate template incubated for seven days in mSBF containing 100 mM $NaHCO_3$.

HAP matrices were observed on the β-TCP template incubated in mSBF containing the varying concentrations of $NaHCO_3$. Incubation of the β-TCP template in mSBF resulted in gradual nucleation and growth of a continuous mineral matrix layer. FIGS. 2A and 2B show matrix layers formed on the surface of a β-TCP template incubated for two days in mSBF containing 4.2 mM $NaHCO_3$. The carbonate concentration in the HAP matrices was varied by varying the concentration of $NaHCO_3$ in the mSBF. The growth of the carbonate matrices over the β-TCP template continued over time. See, FIG. 3 showing coatings formed on the surface of a β-TCP template incubated for seven days in mSBF containing 4.2 mM $NaHCO_3$ (FIGS. 3A and 3B) and 100 mM $NaHCO_3$ (FIGS. 3C and 3D). The $NaHCO_3$ concentration in the mSBF also affected the morphology of the matrix layer. Increasing the $NaHCO_3$ in the mSBF resulted in the formation of smaller spherulites and pores on the β-TCP template (compare, for example, FIGS. 3B and 3D).

Example 4

Figure 4:
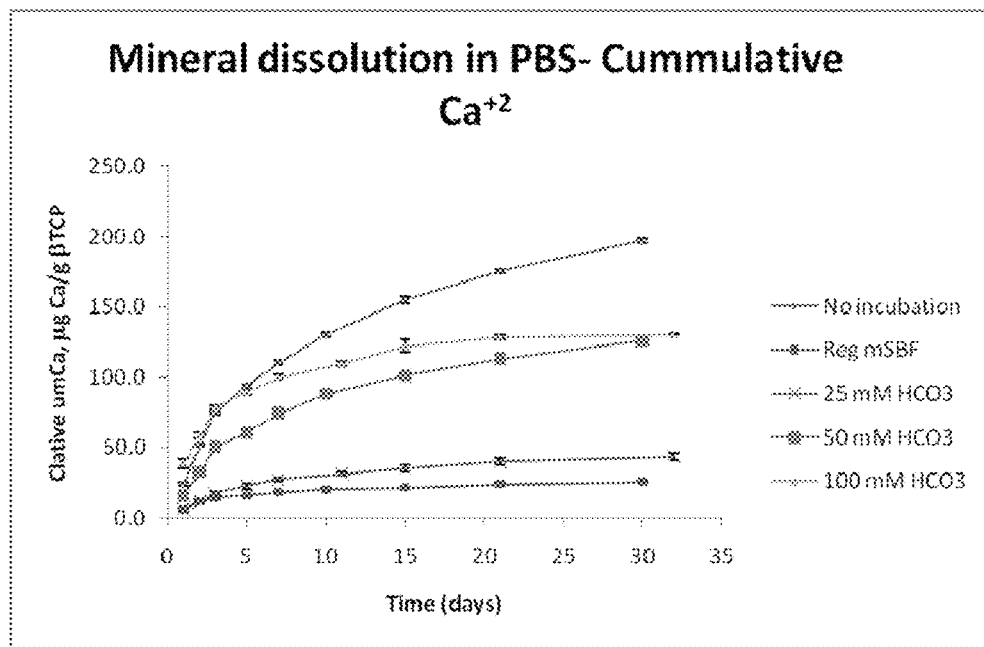
FIG. 4 is a graph illustrating matrix mineral dissolution over time from non-incubated β-tricalcium phosphate and β-tricalcium phosphate template incubated in mSBF containing 4.2 mM (Reg. mSBF), 25 mM, 50 mM, and 100 mM $NaHCO_3$.

Mineral Dissolution from a Tissue Regeneration System Formed Using a β-TCP Template with Hydroxyapatite Matrix Layer In this Example, the cumulative calcium release from a tissue regeneration system formed of a β-TCP template with hydroxyapatite matrix layers was determined. The β-TCP template with HA matrix layers was prepared as described above and the amount of calcium ion released into solution was measured. As shown in FIG. 4, the rate of dissolution of the mineral from the tissue regeneration system prepared using higher carbonate concentrations (e.g., 100 mM $NaHCO_3$) was faster than the rate of dissolution from the tissue regeneration system prepared using lower carbonate concentration (e.g., 4.2 mM $NaHCO_3$ (Reg mSBF), 25 mM $NaHCO_3$, and 50 mM $NaHCO_3$). These results demonstrated that the HAP matrix layer coating stabilized the 3-TCP template since the amount of calcium detected in solution in the control group (e.g., no coating) was greater than the β-TCP template with matrix layers (e.g., 4.2 mM (Reg mSBF), 25 mM, 50 mM, and 100 mM NaHCO$_3$). Additionally, the matrix prepared in mSBF with higher carbonate concentration is less stable, thus resulting in a higher dissolution rate and calcium release.

Figure 5:
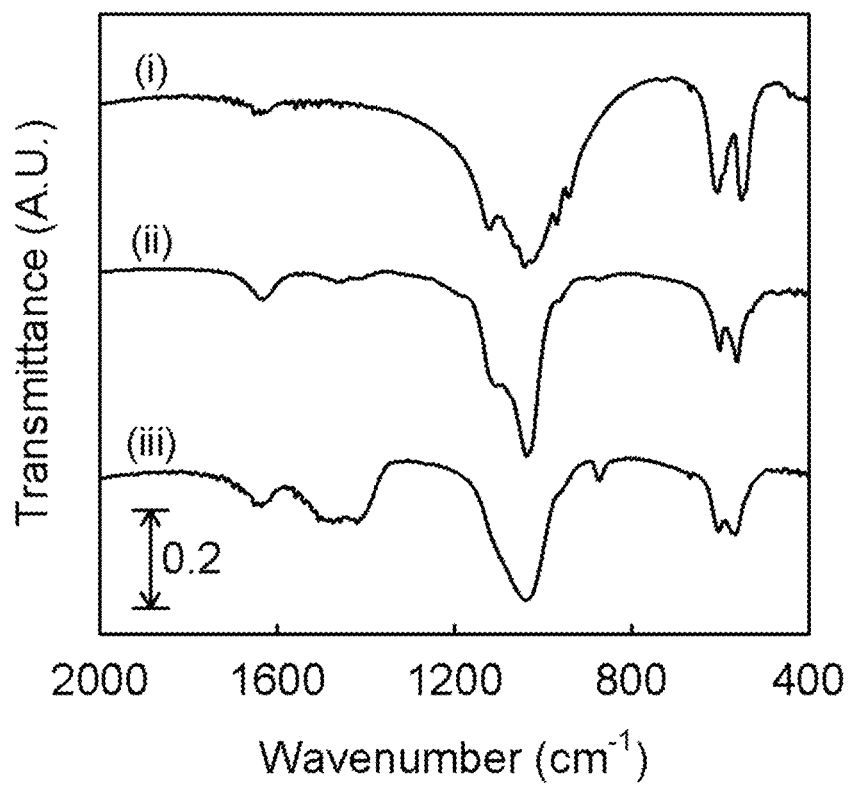
FIG. 5 shows FT-IR spectra of (i) β-tricalcium phosphate template with no matrix layer, (ii) a β-tricalcium phosphate with a matrix layer formed using mSBF containing 4.2 mM $NaHCO_3$, and (iii) β-TCP with a matrix layer formed using mSBF containing 100 mM $NaHCO_3$.

FT-IR spectra was determined for a β-TCP template with matrix layers formed using 100 mM NaHCO$_3$ and 4.2 mM NaHCO$_3$ respectively in mSBF. The increased FT-IR spectra peak observed around 1500-1600 cm$^{-1}$ in curve (iii) for the β-TCP template with the matrix layers formed using 100 mM NaHCO$_3$ indicated a higher carbonation level in the hydroxyapatite matrix layers as compared to the β-TCP template with the matrix layers formed using 4.2 mM NaHCO$_3$ as shown in curve (ii) and β-TCP template with no matrix layer as shown in curve (i). See, FIG. 5. Thus, the degree of carbonation increased when the matrix was formed in mSBF containing higher carbonate concentrations.

Results of the experiments of the tissue regeneration systems formed by coating a β-TCP template with matrix layers using NaHCO$_3$ advantageously permits the rate of mineral dissolution to be controlled. Control of mineral dissolution provides an additional advantage of permitting the controlled delivery of biomolecules during the tissue regeneration process. Further, the tissue regeneration systems formed by coating a β-TCP template according to the instant disclosure are similar in structure and composition to bone mineral allowing for a tissue regeneration system that localizes and temporally controls the release of biomolecules to stimulate tissue regeneration.

While the invention is susceptible to various modifications and alternative forms, specific embodiments thereof have been shown by way of example in the drawings and are herein described below in detail. It should be understood, however, that the description of specific embodiments is not intended to limit the invention to cover all modification, equivalents and alternatives falling within the spirit and scope of the invention as defined by the appended claims.

What is claimed is:

1. A tissue regeneration system comprising:
a porous template consisting of β-tricalcium phosphate and having thereupon at least one synthetic, degradable extracellular matrix layer; and
at least one biomolecule releasably associated with the matrix layer, the biomolecule comprising a cell-affecting portion, wherein the cell-affecting portion is selected from the group consisting of growth factors selected from the group consisting of bone morphogenic protein, fibroblast growth factor, growth differentiation factor, platelet-derived growth factor, placental growth factor, transforming growth factor, insulin-like growth factor, vascular endothelial growth factor, bone sialoprotein, phosphoryn, osteonectin and combinations thereof, wherein the growth factor is capable of initiating at least one of osteogenesis, neovascularization, endothelial differentiation, and osteogenic differentiation, and fragments of growth factors selected from the group consisting of bone morphogenic protein, fibroblast growth factor, growth differentiation factor, platelet-derived growth factor, placental growth factor, transforming growth factor, insulin-like growth factor, vascular endothelial growth factor, bone sialoprotein, phosphoryn, osteonectin and combinations thereof, wherein the fragments are capable of initiating at least one of osteogenesis, neovascularization, endothelial differentiation, and osteogenic differentiation; and
a matrix-binding portion, wherein the matrix-binding portion is selected from the group consisting of SEQ ID NO:1, SEQ ID NO:2, SEQ ID NO:3, SEQ ID NO:12, SEQ ID NO:13, SEQ ID NO:14, SEQ ID NO:15, SEQ ID NO:16, and SEQ ID NO:17.

2. The tissue regeneration system of claim 1, wherein the at least one synthetic, degradable extracellular matrix layer comprises ions of a mineral.

3. The tissue regeneration system of claim 1, wherein the at least one synthetic, degradable extracellular matrix layer is selected from the group consisting of calcium, phosphorus, carbonate, and combinations thereof.

4. The tissue regeneration system of claim 1, wherein the at least one synthetic degradable extracellular matrix layer is selected from the group consisting of hydroxyapatite, alpha-tricalcium phosphate, amorphous calcium phosphate, dicalcium phosphate, octacalcium phosphate, carbonate-substituted hydroxyapatite, and calcium carbonate.

5. The tissue regeneration system of claim 1, wherein the cell-affecting portion is a peptide derived from one of bone morphogenic protein, fibroblast growth factor, vascular endothelial growth factor, growth differentiation factor, platelet-derived growth factor, placental growth factor, transforming growth factor, and insulin-like growth factor.

6. The tissue regeneration system of claim 5, wherein the cell-affecting portion is an amino acid sequence selected from the group consisting of SEQ ID NO:4, SEQ ID NO:5, SEQ ID NO:6, SEQ ID NO:7, SEQ ID NO:8, and SEQ ID NO:9.

7. The tissue regeneration system of claim 1, wherein the biomolecule further comprises a spacer portion.

8. The tissue regeneration system of claim 7, wherein the spacer portion is an amino acid sequence capable of forming an α-helix.

9. The tissue regeneration system of claim 7, wherein the spacer portion is selected from the group consisting of polyethylene glycol, SEQ ID NO:10, SEQ ID NO:11, and one of $(A)_n$, $(E)_n$, $(K)_n$, and $(L)_n$, wherein n is an integer between 1 and 8.

10. A method of coating a template with a degradable extracellular matrix layer comprising at least one biomolecule, the method comprising:
    forming the degradable extracellular matrix layer comprising:
        exposing ions of an inorganic mineral in a solution at a physiological temperature and pH to the template until an inorganic mineral matrix layer is deposited on the surface; and
        exposing at least one species of biomolecule having a cell-affecting portion and a matrix-binding portion to the layer until the layer has associated therewith the at least one species of biomolecule,
    wherein the template consists of β-tricalcium phosphate;
    wherein the cell-affecting portion is selected from the group consisting of growth factors selected from the group consisting of bone morphogenic protein, fibroblast growth factor, growth differentiation factor, platelet-derived growth factor, placental growth factor, transforming growth factor, insulin-like growth factor, vascular endothelial growth factor, bone sialoprotein, phosphoryn, osteonectin and combinations thereof, wherein the growth factor is capable of initiating at least one of osteogenesis, neovascularization, endothelial differentiation, and osteogenic differentiation, and fragments of growth factors selected from the group consisting of bone morphogenic protein, fibroblast growth factor, growth differentiation factor, platelet-derived growth factor, placental growth factor, transforming growth factor, insulin-like growth factor, vascular endothelial growth factor, bone sialoprotein, phosphoryn, osteonectin and combinations thereof, wherein the fragments are capable of initiating at least one of osteogenesis, neovascularization, endothelial differentiation, and osteogenic differentiation; and
    wherein the matrix-binding portion is selected from the group consisting of SEQ ID NO:1, SEQ ID NO:2, SEQ ID NO:3, SEQ ID NO:12, SEQ ID NO:13, SEQ ID NO:14, SEQ ID NO:15, SEQ ID NO:16, and SEQ ID NO:17.

11. The method of claim 10, wherein the mineral is selected from the group consisting of hydroxyapatite, alpha-tricalcium phosphate, amorphous calcium phosphate, dicalcium phosphate, octacalcium phosphate and calcium carbonate.

12. The method of claim 10, wherein the inorganic mineral is exposed to the template for a time period of from about 3 days to about 20 days.

13. The method of claim 10, wherein the cell-affecting portion is selected from the group consisting of SEQ ID NO:4, SEQ ID NO:5, SEQ ID NO:6, SEQ ID NO:7, SEQ ID NO:8, and SEQ ID NO:9.

14. The method of claim 10, wherein the at least one species of biomolecule having a cell-affecting portion and matrix-binding portion further comprises a spacer portion.

15. A method of modulating the degradation rate of a porous template of β-tricalcium phosphate comprising:
    coating the porous template of β-tricalcium phosphate with at least one degradable extracellular matrix layer comprising at least one biomolecule according to the method of claim 10 and
    modulating the degradation rate by controlling dissolution of the at least one degradable extracellular matrix layer.

* * * * *

SEQUENCE LISTING

```
<160> NUMBER OF SEQ ID NOS: 19

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Glu Pro Arg Arg Glu Val Cys Glu Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Glu Glu Glu Glu Glu Glu Glu Glu
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3

Asp Asp Asp Asp Asp Asp Asp Asp
1               5

<210> SEQ ID NO 4
<211> LENGTH: 396
<212> TYPE: PRT
<213> ORGANISM: Homo sapiens

<400> SEQUENCE: 4

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30
```

```
Phe Ala Ala Ala Ser Ser Gly Arg Pro Ser Ser Gln Pro Ser Asp Glu
            35                  40                  45

Val Leu Ser Glu Phe Glu Leu Arg Leu Leu Ser Met Phe Gly Leu Lys
 50                  55                  60

Gln Arg Pro Thr Pro Ser Arg Asp Ala Val Pro Pro Tyr Met Leu
 65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
                100                 105                 110

His His Glu Glu Ser Leu Glu Leu Pro Glu Thr Ser Gly Lys Thr
                115                 120                 125

Thr Arg Arg Phe Phe Phe Asn Leu Ser Ser Ile Pro Thr Glu Glu Phe
                130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
                180                 185                 190

Asp Thr Arg Leu Val Asn Gln Asn Ala Ser Arg Trp Glu Ser Phe Asp
                195                 200                 205

Val Thr Pro Ala Val Met Arg Trp Thr Ala Gln Gly His Ala Asn His
                210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
                260                 265                 270

Gly His Pro Leu His Lys Arg Glu Lys Arg Gln Ala Lys His Lys Gln
                275                 280                 285

Arg Lys Arg Leu Lys Ser Ser Cys Lys Arg His Pro Leu Tyr Val Asp
                290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
                340                 345                 350

Asn Ser Lys Ile Pro Lys Ala Cys Cys Val Pro Thr Glu Leu Ser Ala
                355                 360                 365

Ile Ser Met Leu Tyr Leu Asp Glu Asn Glu Lys Val Val Leu Lys Asn
370                 375                 380

Tyr Gln Asp Met Val Val Glu Gly Cys Gly Cys Arg
385                 390                 395

<210> SEQ ID NO 5
<211> LENGTH: 288
<212> TYPE: PRT
<213> ORGANISM: Homo sapiens

<400> SEQUENCE: 5

Met Val Gly Val Gly Gly Gly Asp Val Glu Asp Val Thr Pro Arg Pro
```

```
              1               5                  10                 15
            Gly Gly Cys Gln Ile Ser Gly Arg Ala Ala Arg Gly Cys Asn Gly Ile
                            20                 25                 30

Pro Gly Ala Ala Ala Trp Glu Ala Ala Leu Pro Arg Arg Arg Pro Arg
                            35                 40                 45

Arg His Pro Ser Val Asn Pro Arg Ser Arg Ala Ala Gly Ser Pro Arg
                        50                 55                 60

Thr Arg Gly Arg Arg Thr Glu Glu Arg Pro Ser Gly Ser Arg Leu Gly
             65                 70                 75                 80

Asp Arg Gly Arg Gly Arg Ala Leu Pro Gly Gly Arg Leu Gly Gly Arg
                            85                 90                 95

Gly Arg Gly Arg Ala Pro Glu Arg Val Gly Gly Arg Gly Arg Gly Arg
                           100                105                110

Gly Thr Ala Ala Pro Arg Ala Ala Pro Ala Ala Arg Gly Ser Arg Pro
                           115                120                125

Gly Pro Ala Gly Thr Met Ala Ala Gly Ser Ile Thr Thr Leu Pro Ala
                           130                135                140

Leu Pro Glu Asp Gly Gly Ser Gly Ala Phe Pro Pro Gly His Phe Lys
            145                150                155                160

Asp Pro Lys Arg Leu Tyr Cys Lys Asn Gly Gly Phe Phe Leu Arg Ile
                           165                170                175

His Pro Asp Gly Arg Val Asp Gly Val Arg Glu Lys Ser Asp Pro His
                           180                185                190

Ile Lys Leu Gln Leu Gln Ala Glu Glu Arg Gly Val Val Ser Ile Lys
                           195                200                205

Gly Val Cys Ala Asn Arg Tyr Leu Ala Met Lys Glu Asp Gly Arg Leu
                           210                215                220

Leu Ala Ser Lys Cys Val Thr Asp Glu Cys Phe Phe Phe Glu Arg Leu
            225                230                235                240

Glu Ser Asn Asn Tyr Asn Thr Tyr Arg Ser Arg Lys Tyr Thr Ser Trp
                           245                250                255

Tyr Val Ala Leu Lys Arg Thr Gly Gln Tyr Lys Leu Gly Ser Lys Thr
                           260                265                270

Gly Pro Gly Gln Lys Ala Ile Leu Phe Leu Pro Met Ser Ala Lys Ser
                           275                280                285

<210> SEQ ID NO 6
<211> LENGTH: 431
<212> TYPE: PRT
<213> ORGANISM: Homo sapiens

<400> SEQUENCE: 6

Met His Val Arg Ser Leu Arg Ala Ala Ala Pro His Ser Phe Val Ala
 1               5                  10                 15

Leu Trp Ala Pro Leu Phe Leu Leu Arg Ser Ala Leu Ala Asp Phe Ser
                20                 25                 30

Leu Asp Asn Glu Val His Ser Ser Phe Ile His Arg Arg Leu Arg Ser
            35                 40                 45

Gln Glu Arg Arg Glu Met Gln Arg Glu Ile Leu Ser Ile Leu Gly Leu
         50                 55                 60

Pro His Arg Pro Arg Pro His Leu Gln Gly Lys His Asn Ser Ala Pro
 65                 70                 75                 80

Met Phe Met Leu Asp Leu Tyr Asn Ala Met Ala Val Glu Glu Gly Gly
                85                 90                 95
```

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
        130                 135                 140

Glu Phe Phe His Pro Arg Tyr His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 7
<211> LENGTH: 412
<212> TYPE: PRT
<213> ORGANISM: Homo sapiens

<400> SEQUENCE: 7

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ala Ser Arg Gly Gln
            20                  25                  30

Gly Pro Glu Pro Ala Pro Gly Gly Gly Val Glu Gly Val Gly Ala Arg
        35                  40                  45

Gly Val Ala Leu Lys Leu Phe Val Gln Leu Gly Cys Ser Arg Phe
 50                  55                  60

Gly Gly Ala Val Val Arg Ala Gly Glu Ala Glu Pro Ser Gly Ala Ala
 65                  70                  75                  80

Arg Ser Ala Ser Ser Gly Arg Glu Glu Pro Gln Pro Glu Glu Gly Glu
                 85                  90                  95

Glu Glu Glu Glu Lys Glu Glu Glu Arg Gly Pro Gln Trp Arg Leu Gly
                100                 105                 110

Ala Arg Lys Pro Gly Ser Trp Thr Gly Glu Ala Ala Val Cys Ala Asp
            115                 120                 125

Ser Ala Pro Ala Ala Arg Ala Pro Gln Ala Leu Ala Arg Ala Ser Gly
        130                 135                 140

Arg Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
                260                 265                 270

Glu Cys Val Pro Thr Glu Glu Ser Asn Ile Thr Met Gln Ile Met Arg
            275                 280                 285

Ile Lys Pro His Gln Gly Gln His Ile Gly Glu Met Ser Phe Leu Gln
        290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Tyr Val Gly Ala Arg Cys Cys
            340                 345                 350

Leu Met Pro Trp Ser Leu Pro Gly Pro His Pro Cys Gly Pro Cys Ser
        355                 360                 365

Glu Arg Arg Lys His Leu Phe Val Gln Asp Pro Gln Thr Cys Lys Cys
370                 375                 380

Ser Cys Lys Asn Thr Asp Ser Arg Cys Lys Ala Arg Gln Leu Glu Leu
385                 390                 395                 400

Asn Glu Arg Thr Cys Arg Cys Asp Lys Pro Arg Arg
                405                 410

<210> SEQ ID NO 8
<211> LENGTH: 20
<212> TYPE: PRT
<213> ORGANISM: Artificial Sequence
<220> FEATURE:
<223> OTHER INFORMATION: Synthetic

<400> SEQUENCE: 8

```
Lys Ile Pro Lys Ala Ser Ser Val Pro Thr Glu Leu Ser Ala Ile Ser
1               5                   10                  15

Thr Leu Tyr Leu
            20

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Lys Leu Thr Trp Gln Glu Leu Tyr Gln Leu Lys Tyr Lys Gly Ile
1               5                   10                  15

<210> SEQ ID NO 10
<211> LENGTH: 4
<212> TYPE: PRT
<213> ORGANISM: Artificial Sequence
<220> FEATURE:
<223> OTHER INFORMATION: Synthetic

<400> SEQUENCE: 10

Ala Ala Ala Ala
1

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Gly Gly Gly Ala Ala Ala Ala
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = gamma-Carboxyglutamic acid
<220> FEATURE:
<221> NAME/KEY: MISC_FEATURE
<222> LOCATION: (5)..(5)
<223> OTHER INFORMATION: X = gamma-Carboxyglutamic acid
<220> FEATURE:
<221> NAME/KEY: MISC_FEATURE
<222> LOCATION: (8)..(8)
<223> OTHER INFORMATION: X = gamma-Carboxyglutamic acid

<400> SEQUENCE: 12

Xaa Pro Arg Arg Xaa Val Ala Xaa Leu
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: X = gamma-Carboxyglutamic acid
<220> FEATURE:
<221> NAME/KEY: MISC_FEATURE
<222> LOCATION: (8)..(8)
<223> OTHER INFORMATION: X = gamma-Carboxyglutamic acid

<400> SEQUENCE: 13

Xaa Pro Arg Arg Ala Val Ala Xaa Leu
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = gamma-Carboxyglutamic acid

<400> SEQUENCE: 14

Xaa Pro Arg Arg Ala Val Ala Ala Leu
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Glu Pro Arg Arg Glu Val Ala Glu Leu
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Glu Pro Arg Arg Ala Val Ala Glu Leu
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

Glu Pro Arg Arg Ala Val Ala Ala Leu
1               5

<210> SEQ ID NO 18
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (21)..(21)
```

```
<223> OTHER INFORMATION: X = gamma-Carboxyglutamic acid
<220> FEATURE:
<221> NAME/KEY: MISC_FEATURE
<222> LOCATION: (25)..(25)
<223> OTHER INFORMATION: X = gamma-Carboxyglutamic acid
<220> FEATURE:
<221> NAME/KEY: MISC_FEATURE
<222> LOCATION: (28)..(28)
<223> OTHER INFORMATION: X = gamma-Carboxyglutamic acid

<400> SEQUENCE: 18

Lys Ile Pro Lys Ala Ser Ser Val Pro Thr Glu Leu Ser Ala Ile Ser
1               5                   10                  15

Thr Leu Tyr Leu Xaa Pro Arg Arg Xaa Val Ala Xaa Leu
            20                  25

<210> SEQ ID NO 19
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (25)..(25)
<223> OTHER INFORMATION: X = gamma-Carboxyglutamic acid
<220> FEATURE:
<221> NAME/KEY: MISC_FEATURE
<222> LOCATION: (29)..(29)
<223> OTHER INFORMATION: X = gamma-Carboxyglutamic acid
<220> FEATURE:
<221> NAME/KEY: MISC_FEATURE
<222> LOCATION: (32)..(32)
<223> OTHER INFORMATION: X = gamma-Carboxyglutamic acid

<400> SEQUENCE: 19

Lys Ile Pro Lys Ala Ser Ser Val Pro Thr Glu Leu Ser Ala Ile Ser
1               5                   10                  15

Thr Leu Tyr Leu Ala Ala Ala Ala Xaa Pro Arg Arg Xaa Val Ala Xaa
            20                  25                  30

Leu
```